United States Patent
Kiuchi et al.

[11] Patent Number: 5,903,006
[45] Date of Patent: May 11, 1999

[54] LIQUID CONCENTRATION DETECTING APPARATUS

[75] Inventors: Norihiro Kiuchi, 4-7 Kinugaoka 2-chome, Hachioji-shi, Tokyo; Kunimitsu Tamura; Seiki Tsurudo, both of Saitama-ken, all of Japan

[73] Assignee: Norihiro Kiuchi, Tokyo, Japan

[21] Appl. No.: 08/863,139

[22] Filed: May 27, 1997

[30] Foreign Application Priority Data

May 31, 1996 [JP] Japan .................................... 8-160539
May 22, 1997 [JP] Japan .................................... 9-147044

[51] Int. Cl.[6] .................................................. G01N 21/35
[52] U.S. Cl. ...................... 250/339.12; 250/343; 250/345
[58] Field of Search ........................ 250/339.12, 339.03, 250/343, 345

[56] References Cited

U.S. PATENT DOCUMENTS

| | | |
|---|---|---|
| 4,492,868 | 1/1985 | Jelvestam et al. ...................... 250/343 |
| 4,633,087 | 12/1986 | Rosenthal et al. .................. 250/339.12 |
| 4,857,735 | 8/1989 | Noller ...................................... 250/343 |
| 5,047,639 | 9/1991 | Wong ...................................... 250/343 |
| 5,075,550 | 12/1991 | Miller et al. ............................ 250/343 |
| 5,173,749 | 12/1992 | Tell et al. ................................ 250/343 |
| 5,267,152 | 11/1993 | Yang et al. ......................... 250/339.12 |
| 5,319,200 | 6/1994 | Rosenthal et al. .................. 250/339.12 |
| 5,585,729 | 12/1996 | Toshima et al. ........................ 324/445 |

FOREIGN PATENT DOCUMENTS

| | | |
|---|---|---|
| 3-175341 | 7/1991 | Japan . |
| 5-187995 | 7/1993 | Japan ..................................... 250/343 |

*Primary Examiner*—Constantine Hannaher
*Assistant Examiner*—Darren M. Jiron
*Attorney, Agent, or Firm*—Seidel, Gonda, Lavorgna & Monaco, PC

[57] ABSTRACT

A liquid concentration detecting apparatus which permits a real-time and high-accuracy detection of concentration of a liquid (particularly an etching or cleaning solution) used in a semiconductor plant, with a simple configuration at a low cost. The liquid concentration detecting apparatus 1 has a cell 2 to which a liquid is supplied, and a projecting section 4 and a receiving section 5 arranged opposite to each other in a direction at right angles to the axial line of the cell. A light of a prescribed wavelength is projected from this projecting section 4 through the liquid in the cell 2 to the receiving section 5, and the concentration of the liquid is determined by detecting the amount of light received by the receiving section. The cell 2 has a plate-shaped spacer 6 having a slender hole 9 formed therein, and at least within a detecting section 3 region where the projecting section 4 and the receiving section 5 are arranged opposite to each other, the cell is configured to be substantially in close contact with the both surfaces of the spacer 6, whereby the liquid supplied to the cell flows in the slender hole 9 formed in the spacer 6 within the detecting section 3.

15 Claims, 12 Drawing Sheets

LED : 1.45 μm, MEASURING TEMP. : 20±0.5°C

LED DRIVING METHOD : 200mA (CONSTANT CURRENT PULSE DRIVING METHOD)

PULSE RATIO : 1.99 (10msec−990msec)

LED : 1.55 μm, MEASURING TEMP. : 20±0.5°C

LED DRIVING METHOD : 100mA (CONSTANT CURRENT PULSE DRIVING METHOD)

PULSE RATIO : 1.99 (10msec—990msec)

LIQUID CONCENTRATION DETECTING APPARATUS

BACKGROUND OF THE INVENTION

The present invention relates to a liquid concentration detecting apparatus which permits real-time and high-precision detection of concentration of a liquid used, for example, in a semiconductor plant, particularly for an etching or cleaning solution, and among others, a fluoric acid-based etching or cleaning solution.

In a semiconductor plant, for example, in order to perform the etching or cleaning of Al, Si or $SiO_2$ as in a semiconductor process or an LSI producing process there are used aqueous solution of various substances such as hydrochloric acid, nitric acid, alkaline etching agents, chromic acid-based etching agents, phosphoric acid, ammonium hydroxide, hydrogen peroxide solution, and mixed water/organic liquid solution (for example, aqueous acetic acid solution), further including such etching or cleaning solutions (hereinafter, generically referred to as "etching solution(s)" as hydrofluoric acid (HF), buffered hydrofluoric acid (BHF), fluoronitric acid and sulfuric acid ($H_2SO_4$). It is required to control the concentration of these etching solutions to ±0.1% in the case where the concentration of the etching solutions is 0 to 10%, and to ±0.01% in the case where the concentration of the etching solutions is 0 to 1%, with a view to maintaining etching performance.

As is disclosed in Japanese Patent Application Laid-Open No. H07-113,745, the present inventors have proposed a concentration detecting apparatus for an aqueous solution containing an inorganic chemical such as hydrofluoric acid. This apparatus comprises, as shown in FIG. 13, a detecting tube 200 running through partition walls 201 of a tubular main body 100, and a projecting section 202 and a receiving section 203 provided opposite to each other with the detecting tube 200 in between. As the apparatus detects water by a wavelength region near a wavelength of 1.48 µm, the projecting section 202 has a light source 204 emitting near infrared rays in a specific wavelength zone absorbed by water, i.e., a light within a wavelength range of from 0.75 µm to 2.5 µm. An optical detector 205 for detecting a light having passed through the aqueous solution containing the organic chemical flowing in the detecting tube 200 from the projecting section 204 is arranged in the receiving section 203. The amount of light detected by the optical detector 205 is converted into an electric signal via a detecting circuit and a control section, and displayed on a display as a quantity of water or a concentration in this aqueous solution, or printed in a printer for output.

In the concentration detecting apparatus having the foregoing configuration, however, a light-emitting diode (LED) having an emitting wavelength region within a range of from 1.1 to 1.6 µm or a semiconductor laser diode, within a range of from 1.1 to 1.67 µm is used as the light source 204 of the projecting section 202, and a cylindrical tube, as the detecting tube 200. It is therefore impossible to detect the concentration of an etching solution (amount of water in the solution) at a high accuracy as ±0.1%.

There is at present available no concentration detecting apparatus, as far as the present inventors know, which permits inline real-time detection, which is a main object of the present invention, of the concentration of an etching solution such as hydrofluoric acid, sulfuric acid, fluoronitric acid or buffered hydrofluoric acid at an accuracy of ±0.1%.

As a result of extensive research and experimental efforts, the present inventors obtained the following findings. That is, it is possible to measure the concentration of an etching solution at a high accuracy from absorbance of the etching solution, by irradiating a light having a wavelength within the near infrared region ensuring clear occurrence of light absorption by the solution, and adopting a special configuration of the detecting section as described later.

The present invention has therefore an object to provide a low-cost liquid concentration detecting apparatus having a simple construction, which permits real-time detection at a high accuracy of the concentration of a liquid used in a semiconductor plant or the like, particularly the concentration of an etching solution (hydrofluoric acid-based etching solution among others).

BRIEF SUMMARY OF THE INVENTION

To achieve the foregoing object of the invention, the present inventors carried out a near infrared spectroscopic analysis on various acids used for etching solutions by means of a conventional spectroscopic analyzer. First, an analysis was conducted for hydrochloric acid and sulfuric acid, and the results were as shown in FIGS. 4 and 5 of Japanese Patent Application Laid-Open No. H07-113,745. Absorbance with a wavelength near 1.45 µm, within a wavelength region of from 1.5 to 1.85 µm of from 1.9 to 2.0 µm and with a wavelength in a range of from 2.1 to 2.4 µm was found to vary with the concentration of the solution.

A light transmitting type cell made of a fluororesin was prepared, and aqueous solutions containing hydrofluoric acid (HF) were prepared with concentrations of diluted acid of 4% and 10% to measure an absorbance spectrum for these samples by means of a conventional near infrared analyzer. The results of measurement are shown in FIG. 3. Within a wavelength region of from 1.3 to 1.9 µm. absorbance varies with the acid concentration, and absorbance was found not to vary within a wavelength region of from 0.4 to 1.1 µm.

As a result of careful study on these results, the present inventors successfully developed the liquid concentration detecting apparatus of the present invention. In summary, the present invention provides a liquid concentration detecting apparatus comprising a cell to which a liquid is supplied and a projecting section and a receiving section arranged opposite to each other in a direction at right angles to the axial line of the cell, wherein a light having a wavelength region within a range of from 1.3 to 1.9 µm is projected from the projecting section through the liquid in the cell to the receiving section, and the amount of light received by the receiving section is detected, thereby detecting the liquid concentration. For example, the foregoing cell is provided with a spacer having a slender hole formed therein, and is configured to be substantially in close contact with the both surfaces of the spacer at least within a detecting region where the projecting section and the receiving section are arranged opposite to each other, whereby the liquid supplied to the cell flows through the slender hole formed in the spacer in the detecting section. Preferably, the cell and the spacer are made of fluororesin or polyethylene resin, particularly, ethylene tetrafluoride-propylene hexafluoride copolymer resin.

The foregoing projecting section has a light source emitting a light having a wavelength region within a range of from 1.3 to 1.9 µm. Preferably, this light source emits a light having a central wavelength within a range of from 1.41 to 1.49 µm, a light-emitting diode emitting a light having a central wavelength of 1.45±0.03 µm, or a light-emitting diode or a laser diode emitting a light having a central wavelength of 1.55 µm±0.05 µm. In this case, the optical path length of the light passing through the liquid in the cell or the slender hole of the spacer in the cell or the thickness of the spacer is within a range of from 0.5 to 10 mm when the projecting section is a light-emitting diode emitting a light having a central wavelength of 1.45 $\mu$m±0.03 $\mu$m, or within a range of from 0.5 mm to 10 mm when the projecting section is a light-emitting diode (laser diode) emitting a light having a wavelength of 1.55 $\mu$m±0.05 $\mu$m.

Preferably, the projecting section comprises a light source for emitting a light of a prescribed wavelength, a beam splitter for splitting the light from the light source in a first direction and a second direction, a lens system for projecting the light emitted in the first direction by the beam splitter to the cell, and a light detector for comparison for detecting the light emitted in the second direction by the beam splitter, whereby the light emitted from the light source is controlled to keep the intensity thereof constant based on the signal detected by said light detector for comparison. As required, a short pass filter for cutting the wavelength portion more than a prescribed wavelength of the light emitted from the light source may be provided between the light source and the beamsplitter.

According to another embodiment of the present invention, furthermore, the projecting section is provided with a first light source emitting a light having a wavelength region within a range of from 1.3 to 1.9 $\mu$m and a second light source for comparison emitting a light having a wavelength region within a range of from 0.4 to 1.1 $\mu$m. Preferably, the projecting section is provided with a first light source emitting a light having a central wavelength within a range of from 1.41 to 1.49 $\mu$m or a central wavelength within a range of from 1.54 to 1.85 $\mu$m, and a second light source emitting a light having a central wavelength within a range of from 0.9 to 1.0 $\mu$m. More preferably, the first light source is a light-emitting diode emitting a light having a central wavelength of 1.45 $\mu$m±0.03 $\mu$m, or a light-emitting diode or a laser diode emitting a light having a central wavelength of 1.55 $\mu$m±0.05 $\mu$m, and the second light source is a light-emitting diode emitting a light having a central wavelength of 0.94 $\mu$m±0.05 $\mu$m.

In the present invention, at least the light-emitting diode emitting a light having a central wavelength of 1.45 $\mu$m±0.03 $\mu$m or the light-emitting diode or the laser diode emitting a light having a central wavelength of 1.55 $\mu$m±0.05 $\mu$m are turned on intermittently, and the light-emitting diode has an on-time/off-time ratio within a range of from 1:99 to 1:200 and is turned on intermittently.

Further, the projecting section has a cooling mechanism based on Peltier element, and the cell and the spacer are integrally secured between securing jigs made of a material having a high thermal conductivity.

In the present invention, the liquid is hydrofluoric acid (HF), buffered hydrofluoric acid (BHF), fluoronitric acid, sulfuric acid ($H_2SO_4$), ammonium hydroxide ($NH_4OH$) or a mixed water/organic liquid solution, particularly, the liquid should preferably be used for an etching solution, or a hydrofluoric acid-based etching solution.

In addition, the light-transmitting cell should preferably be made of light-transmitting glass, sapphire, polypropylene resin, polycarbonate resin, or polyethylene terephthalate resin, as well as the above-mentioned fluororesin.

DETAILED DESCRIPTION OF THE INVENTION

Now, the liquid concentration detecting apparatus of the present invention will be described below further in detail with reference to the drawings.

Embodiment 1

Figure 1:
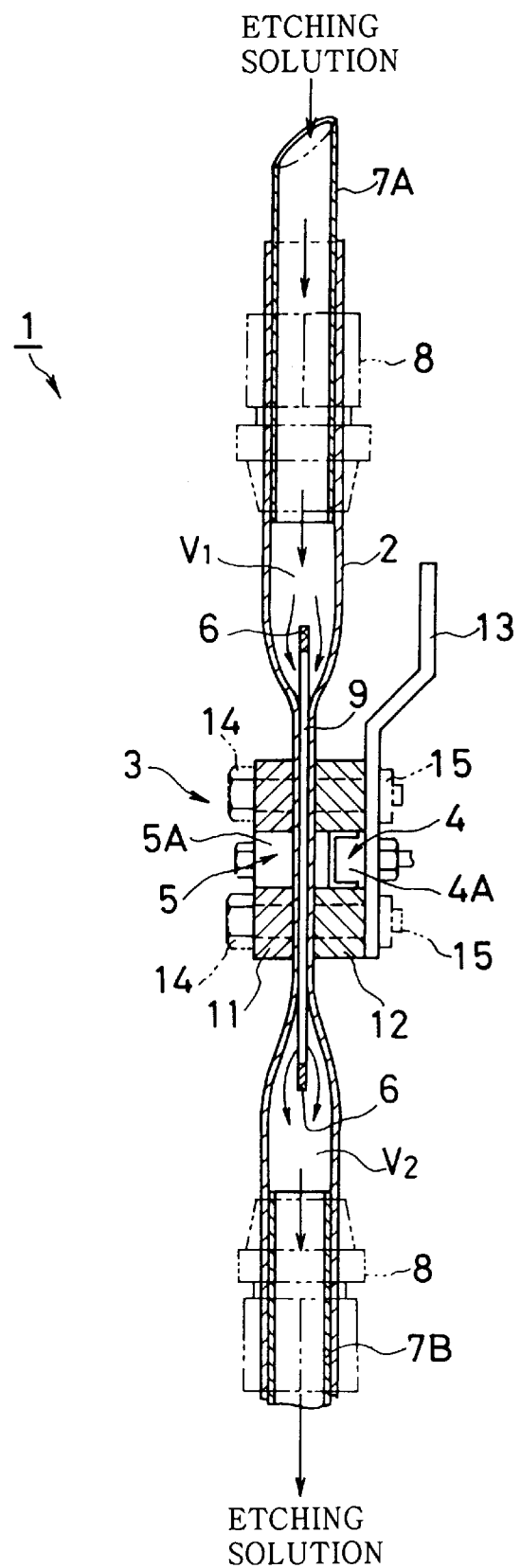
FIG. 1 is a sectional side view of an embodiment of the liquid concentration detecting apparatus of the present invention.
Figure 2:
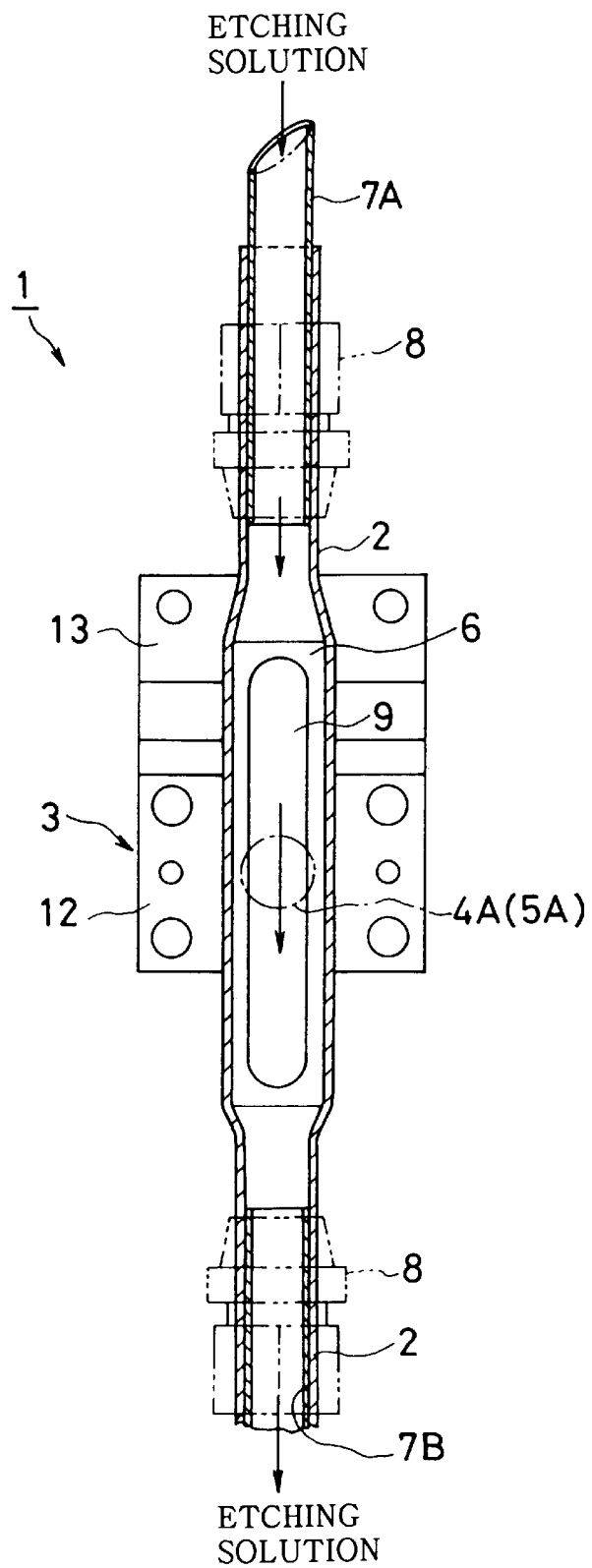
FIG. 2 is another sectional view of the embodiment of the liquid concentration detecting apparatus of the present invention.

An embodiment of the liquid concentration detecting apparatus of the present invention is illustrated in FIGS. 1 and 2. According to this embodiment, the liquid concentration detecting apparatus 1 of the present invention comprises a cell 2 to which a liquid (an etching solution in this embodiment) is supplied, and a projecting section 4 and a receiving section 5 are arranged opposite to each other in a direction at right angles to the axial line of the cell 2 within a region of a detecting section 3 of the cell 2.

According to the present invention, the cell 2 is made of a corrosion-resistant material capable of withstanding a corrosive etching solution such as hydrofluoric acid. As describe later, the material should allow transmission of a light having a wavelength region within a range of from 1.3 to 1.9 μm. Materials satisfying these conditions include a fluororesin and a polyethylene resin. Fluororesins having a high chemical resistance, such as PFA (ethylene tetrafluoride-perfluoroalkylether copolymer resin), FEP (ethylene tetrafluoride-propylene hexafloride copolymer resin), ETFE (ethylene tetrafluoride-ethylene copolymer resin), ECTFE (ethylene trifluorochloride-ethylene copolymer resin), PTFE (ethylene tetrafluoride resin), PCTFE (ethylene trifluoro-chloride resin), PVdF (vinylidene hydrofluoride resin) and VDF (vinyl hydrofluoride resin).

According to the results of research and experiments carried out by the present inventors, FEP (ethylene tetrafluoride-propylene hexafluoride copolymer resin), particularly among other fluororesins, shows a very high transmissivity relative to the foregoing near infrared rays (almost equal to that of glass), is excellent in weldability, and further, can be formed into a hollow tube having a circular cross-section, i.e., a cylindrical tube, thus proving suitable for use in the present invention. In this embodiment, therefore, a flexible tube made of FEP (ethylene tetrafluoride-propylene hexafluoride copolymer resin) having an inside diameter of 9 mm, and a thickness of 0.5 mm is used as a material for the cell 2.

Varying with the kind of liquid, the cell 2 may be made of glass, sapphire, polypropylene resin, polycarbonate resin or polyethylene terephthalate resin.

According to the present invention, furthermore, in the detecting section 3 in which the projecting section 4 and the receiving section 5 are arranged opposite to each other, a plate-shaped spacer 6 is arranged in the cell 2, and the cell 2 takes a flat shape. A slender hole 9 is formed in the spacer 6 at the center. An upper and a lower supporting hollow tubes 7 (7A and 7B) made of hard teflon are inserted into an extension formed at a prescribed distance from the both ends of the spacer 6, for example apart from the both ends thereof by about 2 cm. The FEP tube and the supporting hollow tubes 7A and 7B are integrally secured by an adapter plate 8. The spacer 6 inhibits fluctuations of the width of the liquid in the cell, i.e., fluctuations of the optical path length caused by thermal contraction or deformation of the cell 2 under the effect of a temperature change.

In the present embodiment, tubes made of hard FEP having an outside diameter of 8 mm and a thickness of 1 mm are employed as the supporting hollow tubes 7A and 7B. The spacer 6 comprises a plate made of FEP having a length of 65 mm, a width of 12 mm and a thickness of 1 mm in this embodiment. A slender hole 9 having a length of 60 mm and a width of 8 mm is formed at the center of the spacer 6 in this embodiment.

According to this embodiment, the flat cell 2 having the spacer 6 therein, constituting the detecting section 3, has securing jigs 11 and 12 arranged on the both surfaces thereof. These securing jigs 11 and 12 are mutually tightened by a bolt 14 and a nut 15 in such a manner that the cell 2 and the spacer 6 are held in between. As a result, the securing jigs 11 and 12 and the flat cell 2 having the spacer 6 therein are brought into substantially close contact with each other and integrally secured.

In this embodiment, the securing jigs 11 and 12 should preferably be made of a metallic material excellent in thermal conductivity such as copper or steel and have a length of 30 mm, a width of 40 mm and a thickness of about 7 mm. The shapes and dimensions of the securing jigs are not limited to those in this embodiment, but may be arbitrarily selected. An adapter plate 13 is provided on the securing jig 12 to allow the liquid concentration detecting apparatus 1 to be attached to another prescribed apparatus.

A light source 4A comprising the projecting section 4 is arranged on the securing jig 12. This light source 4A should emit a light having a near infrared region within arange of from 1.3 to 1.9 μm within which light absorption clearly occurs, or emits a light having a central wavelength within a range of from 1.41 to 1.49 μm, or emit a light having a central wavelength within a range of from 1.54 to 1.85 μm.

FEP forming the foregoing cell 2 exhibits a very high permeability relative to such near infrared rays (of the same order as that of glass).

A light detector 5A sensing a light having been projected from the projecting section 4 and transmitted through the etching solution flowing in the cell 2 is arranged in the receiving section 5. A photodiode is suitable as the light detector 5A.

In this embodiment, a light-emitting diode (LED) emitting a light having a central wavelength of 1.45 μm±0.03 μm, and a wavelength region with 50% of the maximum amount of light within a range of from 1.4 to 1.5 μm (made by Shimazu Company; product name: HK-9321) is used as the light source 4A of the projecting section 4, and this gives satisfactory results. Use of a light-emitting diode (LED) emitting a light having a central wavelength of 1.55 μm±0.05 μm and a wavelength region with 50% of the maximum amount of light within a range of from 1.05 to 2.0 μm (made by Oki Denki Company; product name: OE506G) as the light source 4A of the projecting section 4 also gives satisfactory results. Further, use of a laser diode emitting a light having a central wavelength of 1.55 μm or a semiconductor laser emitting a light having a central wavelength of 1.60 μm or 1.67 μm as the light source 4A of the projecting section 4 also gives satisfactory results, but the higher cost of these semiconductor laser as compared with a light-emitting diode (LED) leads to a higher cost of the detecting apparatus. A white light source or an infrared light-emitting element used for an analyzer may also be employed as the light source, and in this case, a light having a wavelength with the above-mentioned ranges is available by means of a spectroscopic filter or a diffraction lattice.

An InGaAs-pin photodiode is used as the light detector 5A of the receiving section 5.

Assume that the projecting section 4 has a light intensity Po and the receiving section 5 receives a light having a light intensity P, then:

$$\text{Absorbance} = \log (Po/P) = kC$$

If Po is assumed to be constant, P depends upon the concentration C of the etching solution. In the above formula, k is a constant intrinsic to an optical system.

Figure 4:
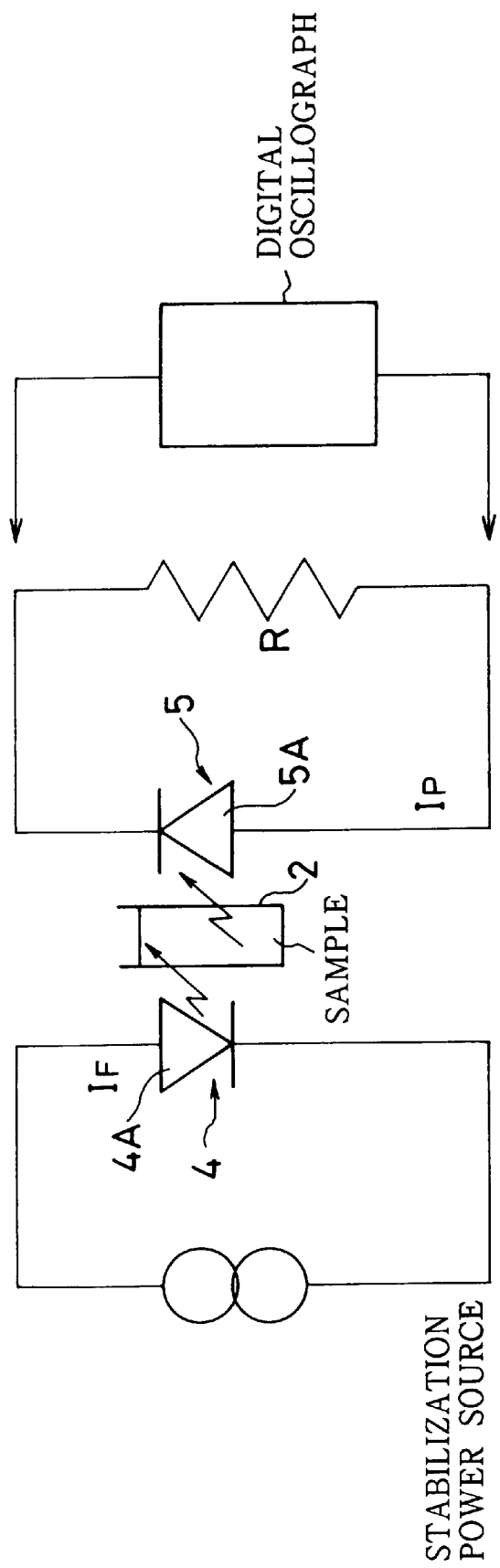
FIG. 4 is a diagram illustrating a configuration of an optical system and a receiving and a projecting circuits of an embodiment for measuring the concentration of a liquid.
Figure 5:
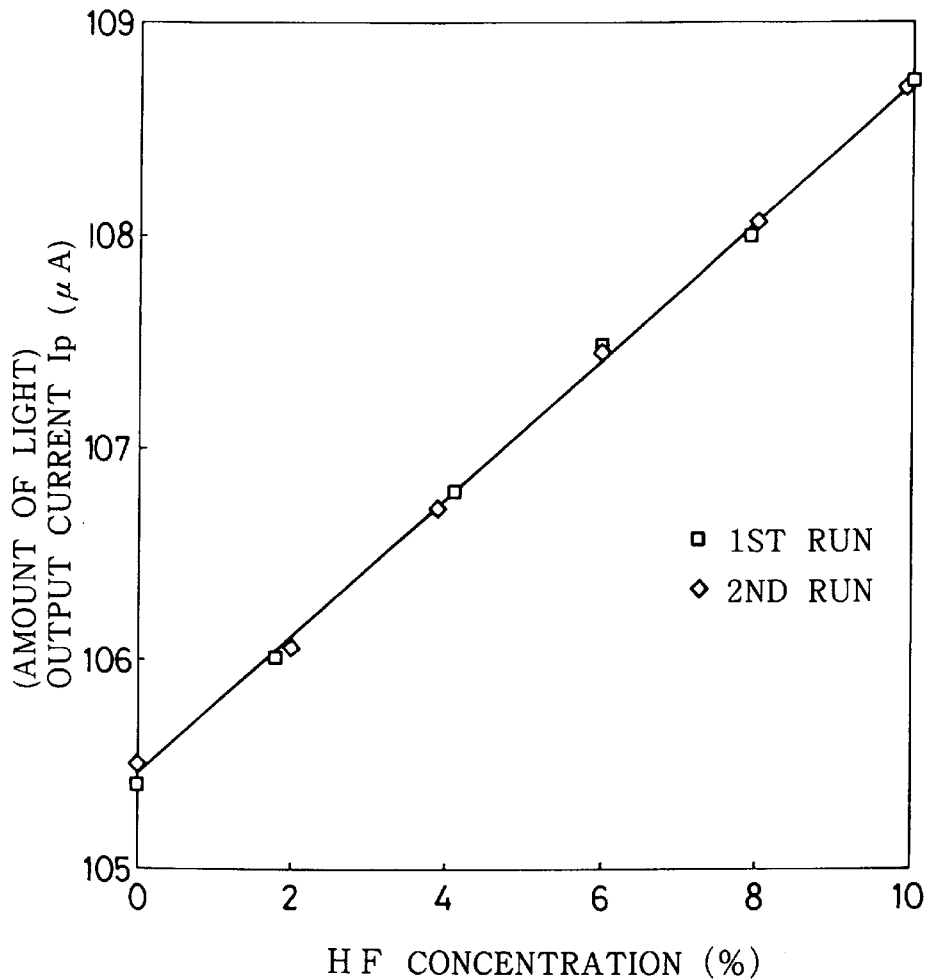
FIG. 5 is a graph illustrating the relationship between the hydrofluoric acid concentration and an output current Ip from the receiving section when using a diode (made by Shimazu Company; product name: HK-9321) having a central wavelength of 1.45 $\mu$m in the configuration shown in FIG. 4.
Figure 6:
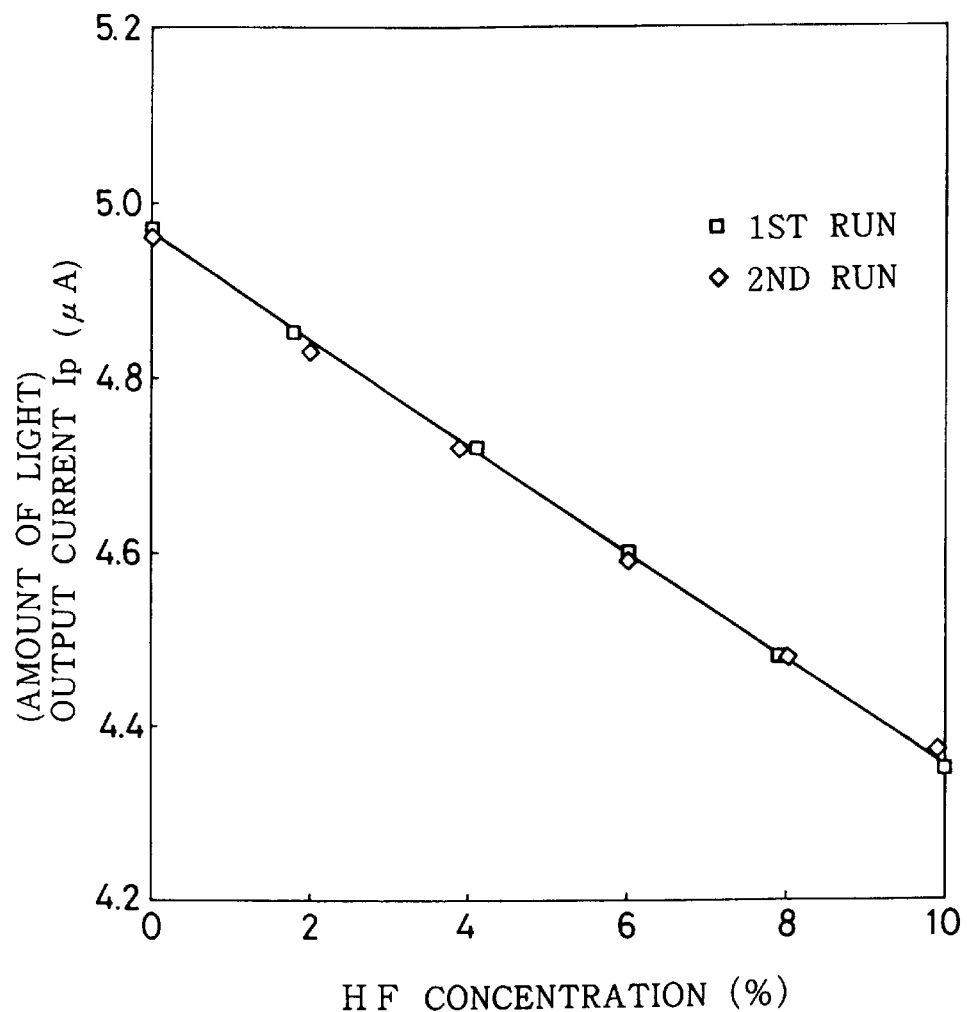
FIG. 6 is a graph illustrating the relationship between the hydrofluoric acid concentration and an output current Ip from the receiving section when using a light-emitting diode (LED) (made by Oki Denki Company; product name: OE506G) having a central wavelength of 1.55 $\mu$m±0.05 $\mu$m.

When measuring the amount of light having passed through the etching solution flowing in the cell at the receiving section 5 receiving a near infrared light of 1.45 μm or 1.55 μm projected from the projecting section 4, there is a correlation between the amount of light detected at the receiving section 5 and the concentration of the liquid (etching solution concentration), as described above. The results of measurement of the relationship between the hydrofluoric acid concentration and the output current Ip from the receiving section 5 at a temperature of 20°±0.5° C. with the use of an aqueous hydrofluoric acid (HF) solution as the etching solution in a circuit configuration as shown in FIG. 4 are shown in FIGS. 5 and 6. Values of output current Ip from the receiving section 5 were obtained by measuring voltage of a resistance R (1 k Ω) with a digital oscillograph and converting the resultant value of voltage into current, and correspond to the light intensity of the light received by the receiving section 5. Reproducibility was confirmed through two runs of measurement by pulse-driving at a constant current the light source 4A (LED light source) of the projecting section 4 so as to give a current of 100 mA and on-time/off-time of 10 msec:990 msec. FIGS. 5 and 6 suggest that a proportional relationship is confirmed between the hydrofluoric acid concentration and the output current Ip from the light detector 5A of the receiving section 5 when the wavelength is 1.45 $\mu$m or 1.55 $\mu$m. Good agreement between the results of the first run and those of the second run of measurement reveals a high reproducibility. The liquid concentration (concentration of the etching solution) is therefore determinable from the amount of light measured at the receiving section 5.

The amount of light sensed by the above-mentioned light detector 5A is converted into an electric signal via a detecting circuit and control section, and is displayed on a display of the display section or printed in a printer for output in the form of a quantity or concentration of the constituent in this aqueous solution.

More specifically, in the concentration detecting apparatus of the present invention, an electronic circuit converting an amount of light received by the light detector 5A into an electric signal can be provided in the receiving section 5. A voltage detecting circuit frequency-converting an amount of light detected by the receiving section light detector 5A, such as the one disclosed in Japanese Patent Application Laid-Open No. H04-324,328 proposed by the present applicant can be appropriately used as the electronic circuit. This voltage detecting circuit will now be briefly described with reference to FIG. 7.

Figure 7:
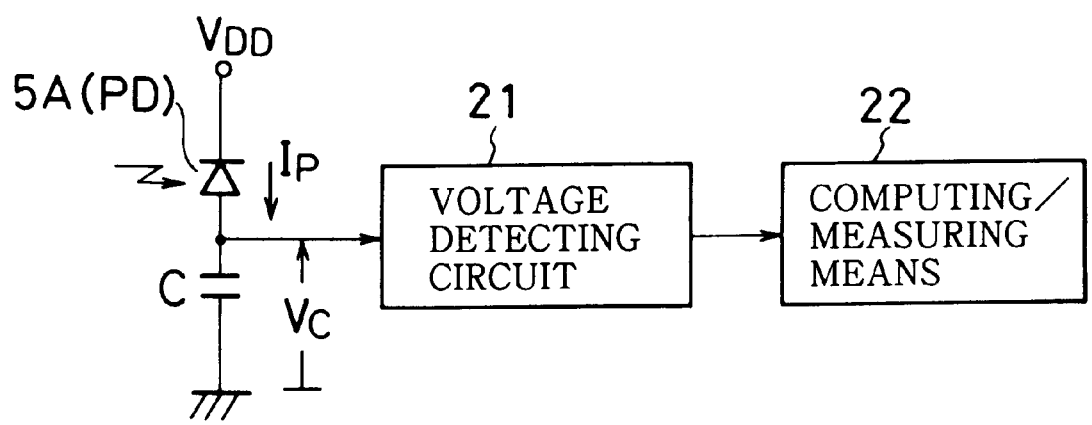
FIG. 7 is a block diagram illustrating an embodiment of an electronic circuit configuration of the liquid concentration detecting apparatus of the present invention.

FIG. 7 is a block diagram illustrating a basic configuration of the voltage detecting circuit 21. In this embodiment, a capacitor C is connected in series to a photodiode PD as the light detector 5A of the receiving section 5. Current Ip fed by the photodiode PD in proportion to the amount of the received light is accumulated in the capacitor C and converted into voltage Vc. This charge voltage Vc is detected in the voltage detecting circuit 21, and compared with a reference voltage set in advance. When the charge voltage reaches the reference voltage, the voltage detecting circuit 21 causes a change in the output signal level. This change in the signal level causes discharge of the electric charge accumulated in the capacitor C, and accumulation of output current Ip from the photodiode PD is started again by the capacitor C. A frequency signal corresponding to the intensity of light received by the receiving section 5 is thus issued from the voltage detecting circuit 21.

The frequency signal from the voltage detecting circuit 21 generated in proportion to the amount of light is computer-processed in computing/measuring means 22, and converted into a pulse count corresponding to the concentration of the etching solution. This output pulse from the computing/measuring means 22 is transmitted to the display section (not shown), and displayed on the display, or printed in the printer for output as a quantity or concentration of the constituent in the etching solution. As required, the display section may have a configuration in which the display has an alarm apparatus to issue an alarm when the concentration of the etching solution reaches a prescribed value.

Now, operations of the concentration detecting apparatus having the above configuration will be described further in detail.

In FIGS. 1 and 2, an upper supporting hollow tube 7A is connected to a supply source of the etching solution to be measured, and a lower supporting hollow tube 7B can be connected to this etching solution source to return the etching solution after measurement back to the etching solution source.

When the etching solution is supplied through the upper supporting hollow tube 7A to the concentration detecting apparatus 1, the etching solution flows into an upper cylindrical space V1 not as yet formed into a flat shape of the cell 2. As is understood from FIGS. 1 and 2, a plate-shaped spacer 6 extends upward and downward from the detecting section 3 region made flat by the securing jigs 11 and 12, and the slender hole 9 of the spacer 6 is formed to extend upward and downward as well from the detecting section 3 region.

Therefore, when the etching solution flows down while being guided by the cell 2 deformed flat to the spacer 6, the etching solution is directed into the slender hole 9 formed at the center of the spacer 6, flows down through the slender hole 9, and passes through the detecting section 3 region. Because the lower portion of the slender hole 9 of the spacer 6 opens toward a cylindrical space V2 below the cell 2, the etching solution is directed into this lower cylindrical space V2 by flowing down, and then, returned through the lower supporting tube 7B back to the etching solution source.

According to the present invention, as described above, the etching solution passes through the detecting section 3 region where the projecting section 4 and the receiving section 5 are arranged opposite to each other, during the process of flowing down in the slender hole 9 of the spacer 6. In the receiving section 5, therefore, the amount of light varies with the concentration of the etching solution. According to the present invention, the distance of the light passage in the cell from the projecting section is equal to the thickness of the spacer 6, and the light can enter the receiving section 5 almost as a parallel beam as irradiated from the projecting section 4. As compared with the use of a cylindrical hollow tube as the cell, it is possible to avoid unnecessary refraction or scattering of the light, and measurement of the amount of light at a high accuracy is achieved without detecting a light (noise) containing information other than the concentration information of the object to be detected at the receiving section 5.

The distance of light passage through the liquid flowing in the slender hole (i.e., the optical path length) should be within a range of from 0.5 to 5.0 mm, or preferably, from 0.7 to 3.0 mm when using a light-emitting diode (LED) emitting a light having a central wavelength of 1.45 $\mu$m±0.03 $\mu$m and a wavelength region within a range of from 1.4 to 1.5 $\mu$m at 50% of the maximum amount of light (made by Shimazu company; product name: HK-9321) as the light source 4A of the projecting section 4. With an optical path length of under 0.5 mm, a large light absorption by aqueous solution leads to a smaller difference in output current of the receiving section 5 between 5% and 0% hydrofluoric acid, thus making it impossible to obtain a sufficient detection sensitivity. With an optical path length of over 5.0 mm, on the other hand, a sufficient output current of the receiving section 5 can not be obtained. An optical path length within a range of from 0.7 to 3.0 mm ensures availability of highly reproducible and stable output current of the receiving section 5.

When using a light-emitting diode (LED) having a central wavelength of 1.55 $\mu$m±0.05 $\mu$m and a wavelength region of from 1.05 to 2.0 $\mu$m at 50% of the maximum amount of light (made by Oki Denki Company; product name: OE506G) as the light source 4A of the projecting section 4, the optical path length should be within a range of from 0.5 to 10 mm, or preferably, from 1 to 5 mm, thus allowing a longer optical path length than in the case described above. This is because of a smaller light absorption by water. In this embodiment, the spacer 6 comprises an FEP plate having a length of 65 mm, a width of 12 mm and a thickness of 2 mm, resulting in an optical path length of 2 mm.

In order to ensure satisfactory operation of the concentration detecting apparatus of the present invention having the construction as described above, as is understood from the above description, it is essential that a wavelength of 1.45 μm±0.03 μm or a wavelength of 1.55 μm±0.05 μm should be constantly irradiated from the light source 4A of the projecting section 4 at a constant intensity to the receiving section 5. The light source 4A is therefore driven by a constant-current power source.

According to the results of research and experiments carried out by the present inventors, however, the light-emitting diodes (LEDs) used in this embodiment (made by Shimazu Company; product name: HK-9321; and made by Oki denki Company; product name: OE506G) were found to involve the following problems.

These light-emitting diodes give a smaller amount of light as compared with conventional light-emitting diodes. In the case of the light-emitting diode (LED (made by Shimazu Company; product name: HK-9321), for example, achievement of an amount of light of 1.5 mW requires a far larger current than in conventional cases, such as about 200 mA. As a result, self heat generation causes an increase in temperature, and the amount of light was found to vary (drop) accordingly. This in turn causes a measuring error.

As a result of further research and experiments carried out to solve this problem, the present inventors found the possibility of solving the problem of the decrease in the amount of light, not by continuously turning on the light-emitting diode, but intermittently turning on the diode, i.e., by inhibiting heat generation through adoption of the pulsation turn-on method.

Figure 8:
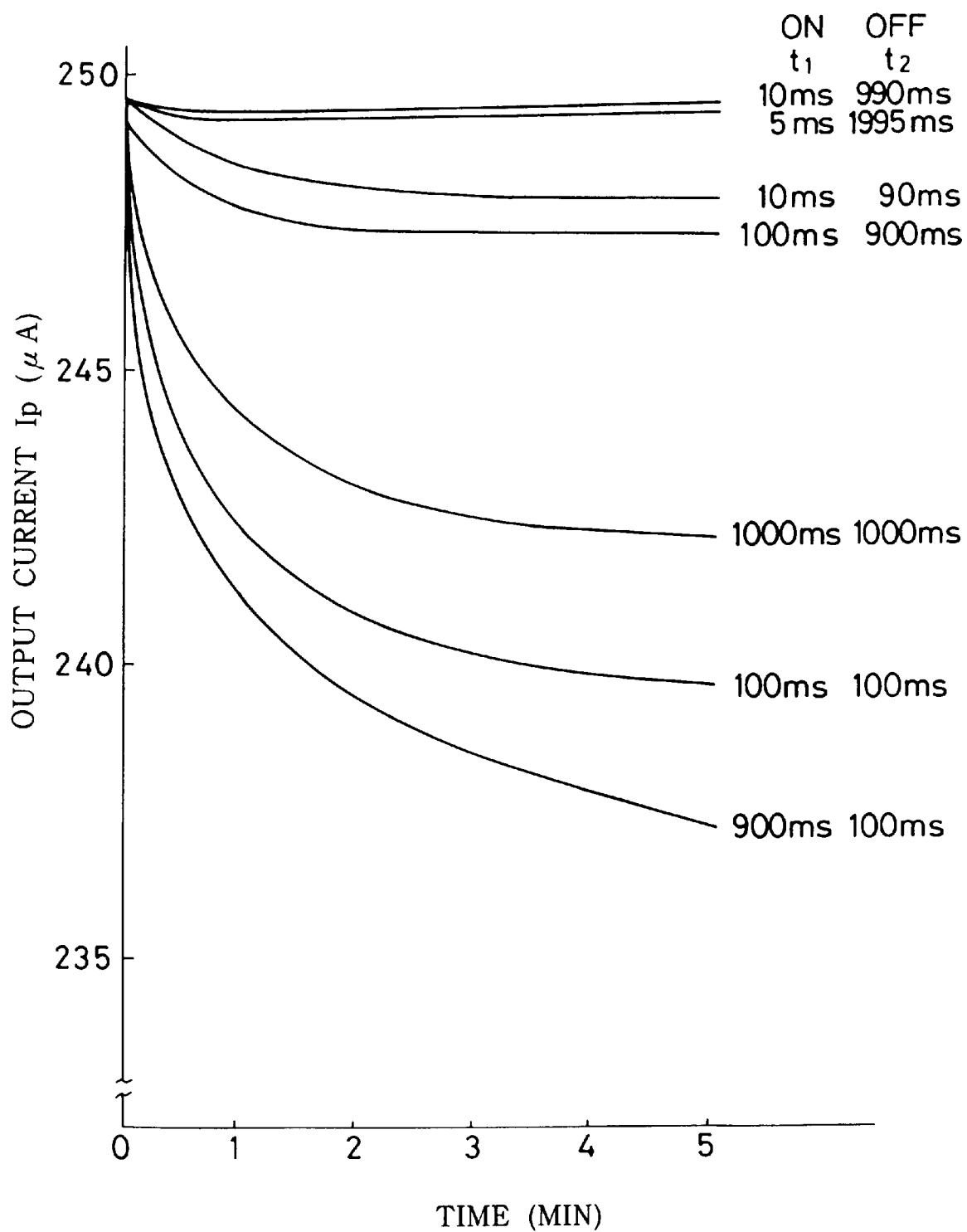
FIG. 8 is a graph illustrating changes in output current Ip from the receiving section at various on-times and off-times of a light-emitting diode (made by Shimazu Company; product name: HK-9321)

Changes in output current Ip from the receiving section 5 were measured by feeding a constant current of 200 mA to a light-emitting diode (LED) (made by Shimazu Company; product name: HK-9321) in the circuit configuration as shown in FIG. 4, and changing the on-time and the off-time to various levels. The results are illustrated in FIG. 8. In the cases with a current of 200 mA, an on-time of 10 mS and an off-time of 990 mS, and with an on-time of 5 mS and an off-time of 1,995 mS, output current Ip (corresponding to the amount of light) from the receiving section 5 showed no substantial decrease with the lapse of time, giving satisfactory results. In the cases with an on-time of 10 mS and an off-time of 90 mS, and with an on-time of 100 mS and an off-time of 900 mS, output current Ip (corresponding to the amount of light) from the receiving section 5 decreased with the lapse of time, giving only poor results. That is, a small ratio of the on-time to the off-time (on-time/off-time) permits inhibition of the decrease in the amount of light of the light-emitting diode. These results suggest that a ratio on-time:off-time within a range of from 1:99 to 1:200 is preferable.

With a view to preventing self heat generation of the light-emitting diode, manufacture of the securing jigs 11 and 12 from a material having a high thermal conductivity is recommendable because of the promotion of heat dissipation, the securing jigs 11 and 12 serving as heat sinks. To further improve heat dissipation, a heat-dissipating silicone resin (for example, made by San-Hayato Company; product name: Heat Resistant and Heat Dissipating Silicone SCH-20) is used as an adhesive between the light-emitting diode and the securing jig 11. Changes in the amount of light with time were compared between a case where the securing jigs 11 and 12 were made of polypropylene poor in thermal conductivity and the light-emitting diode and the securing jig were bonded, on the one hand, and a case where the securing jigs 11 and 12 were made of a metal (copper, for example) having a high thermal conductivity, and the light-emitting diode and the securing jig 11 were bonded with a heat-dissipating silicone resin (made by San-Hayato Company; product name: Heat Resistant and Heat Dissipating Silicone SCH-20), on the other hand. The light-emitting diode emitted a light at a constant current of 200 mA continuously for five minutes. While temperature of the securing jig 11 increased by 30° C. in the case with the securing jigs 11 and 12 manufactured from increase of the securing jig 11 could be inhibited to below 5° C. in the case where the securing jigs 11 and 12 were made of a metal (copper, for example) excellent in thermal conductivity.

By using a light source provided with a cooling mechanism based on Peltier element (for example, a light-emitting diode (LED) made by Oki Denki Company; product names: OE503G and OE506G) as the laser diode or the light-emitting diode used for the light source 4A of the projecting section 4, it is possible to further improve heat dissipation.

By the use of the etching solution concentration detecting apparatus 1 having the construction as described above, concentration of hydrofluoric acid could be continuously measured at an accuracy of ±0.1%.

Embodiment 2

Figure 9:
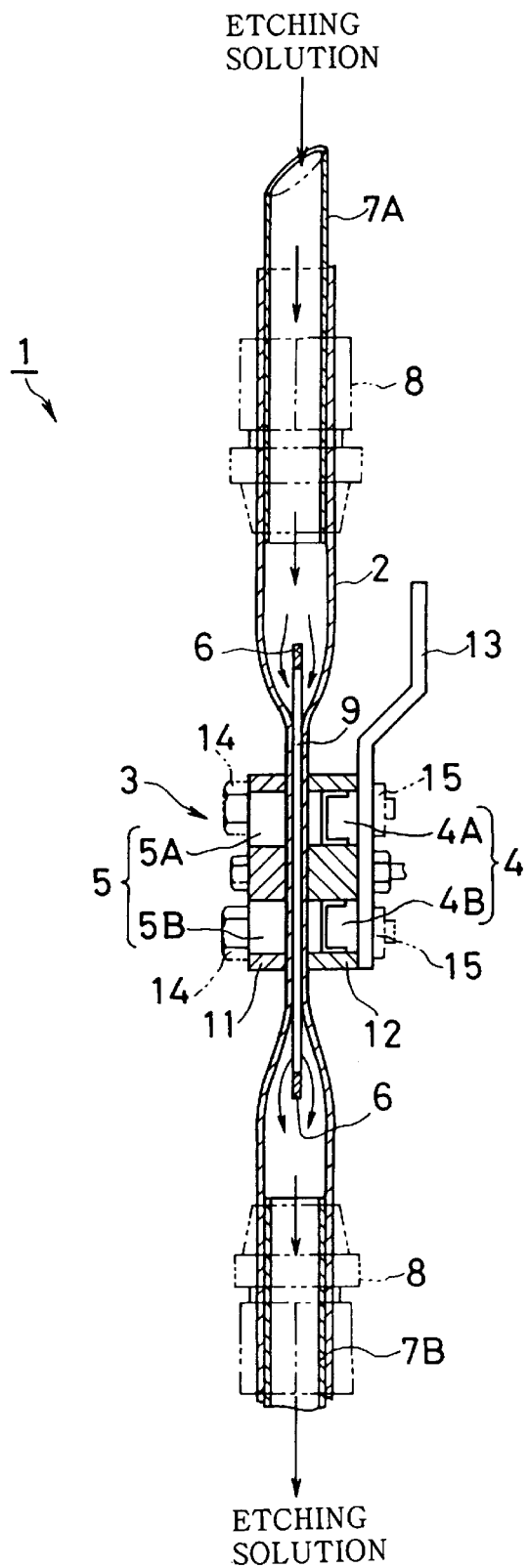
FIG. 9 is a sectional side view of another embodiment of the liquid concentration detecting apparatus of the present invention.

FIG. 9 illustrates another embodiment of the present invention. The liquid concentration detecting apparatus 1 of this embodiment has the same configuration as that of the first embodiment except that a first and a second light sources 4A and 4B are provided in the projecting section 4 composing the detecting section 3, and a first and a second light detectors 5A and 5B are provided similarly in the receiving section 5.

The first light source 4A of the projecting section 4 comprises a light-emitting diode (LED) (made by Oki Denki Company; product name: OE506G) having a central wavelength of 1.55 μm±0.05 μm and a wavelength region within a range of from 1.05 to 2.0 μm at 50% of the maximum amount of light, and the first light detector 5A is the same as the light detector 5A in the first embodiment.

The second light source 4B in this embodiment is a light source for comparison and is used for detecting contamination of the etching solution or bubbles present in the solution, and for correcting measurement of concentration of the etching solution.

The second light source 4B should preferably emit a light within a range of from 0.4 to 1.1 μm, or more preferably, having a central wavelength within a range of from 0.9 to 1.0 μm. In this embodiment, a light-emitting diode (LED) (made by Toshiba Company; product name: TLN110) having a central wavelength of 0.94 μm±0.05 μm and a wavelength region within a range of from 0.915 to 0.96 μm at 50% of the maximum amount of light is used, giving satisfactory results. The second light detector 5B of the receiving section 5 is the same as the light detector 5A in the first embodiment. The second light source 4B may be of the pulsation turn-on type as the first light source 4A. The second light source 4B intermittently emits light with a constant current of 200 mA and a on-time:off-time ratio of 1:99.

The second light source 4B may be appropriately be selected from among a light-emitting diode of a wavelength of 470 nm in the visible region, a light-emitting diode of 560 nm and a light-emitting diode of 660 nm as required, depending upon absorption spectrum of contamination within the visible region (wavelength: 0.4 to 0.7 μm).

The liquid concentration detecting apparatus of this embodiment permits continuous measurement of the hydrofluoric acid concentration at an accuracy of ±0.1%.

Embodiment 3

Figure 10:
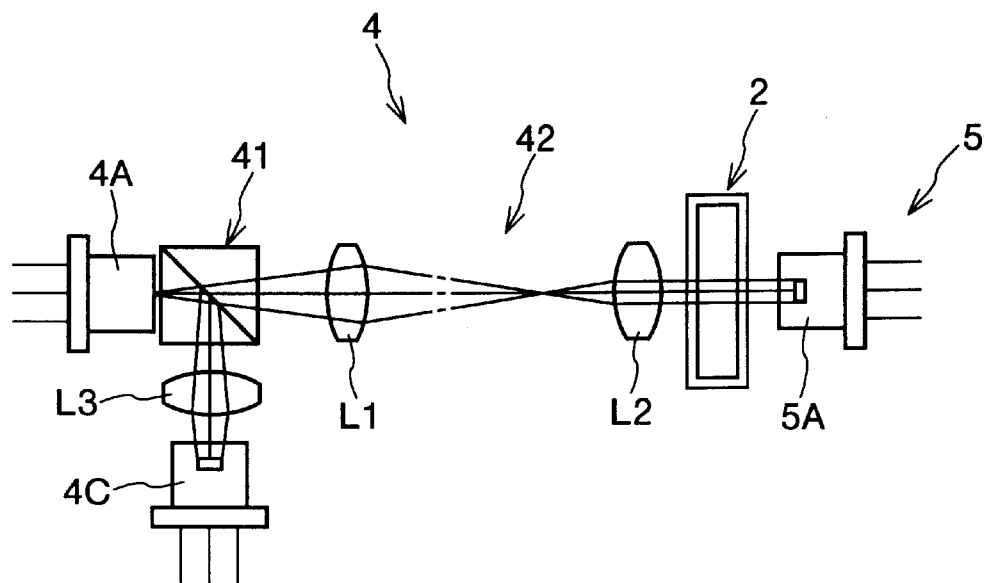
FIG. 10 is a schematic configuration diagram of an embodiment of the projecting section of the liquid concentration detecting apparatus of the present invention.
Figure 11:
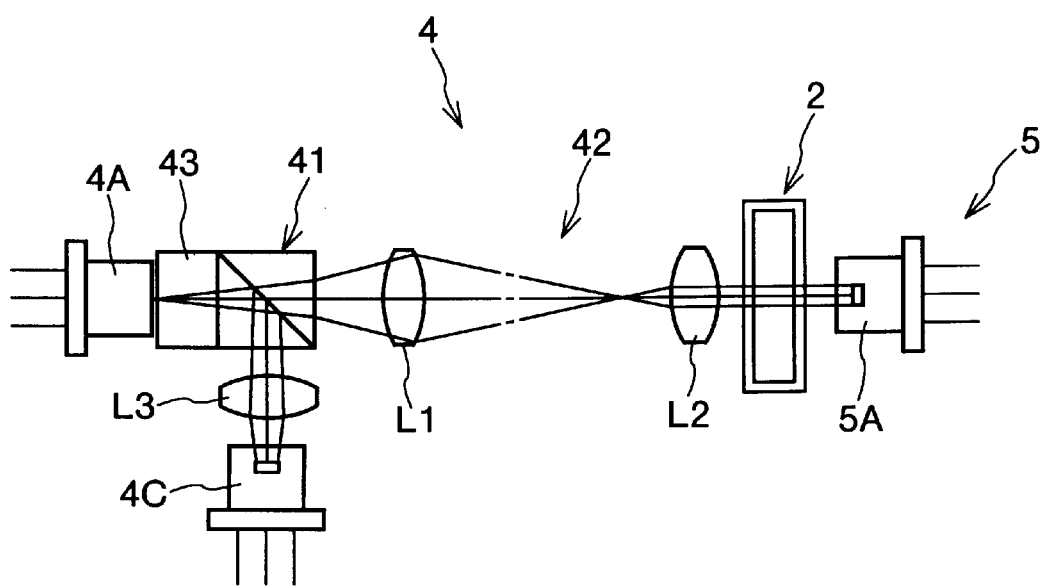
FIG. 11 is a schematic configuration diagram of another embodiment of the projecting section having substantially the same configuration as that shown in FIG. 10.

FIGS. 10 and 11 illustrate further another embodiment of the detecting section 3 applicable for the liquid concentration detecting apparatus of the present invention.

In order for the liquid concentration detecting apparatus of the first embodiment to operate satisfactorily, as described above, a light of a prescribed wavelength must always be irradiated with a constant intensity from the light source 4A of the projecting section 4 through the cell 2 to the receiving section 5.

According to the results of research and experiments carried out by the present inventors, in order to detect the concentration of an etching solution having a low concentration as 0 to 1%, in particular, it is necessary for the light source 4A to control fluctuations of the amount of light at a higher accuracy. A conceivable solution is to drive the light source 4A at a high accuracy with a constant-current power source. There is however a problem that such a constant-current power source leads to a more complicated equipment configuration and a larger size of apparatus. This problem was successfully solved by adopting the configuration shown in FIG. 10 for the projecting section 4.

More specifically, in this embodiment, the light from the light source 4A of the projecting section 4 is irradiated via a beam splitter (half mirror) 41 and a lens system 42 onto the cell 2. The light having passed through the liquid flowing in the cell 2 is detected at the receiving section 5 in the same manner as in the foregoing embodiment. The lens system 42 projects the incident light from the beam splitter 41 as a parallel beam to the cell, and is composed of, but not limited to, convex lenses L1 and L2.

According to this embodiment, furthermore, part of the light from the light source 4A is taken out at the beam splitter 41 and detected through the lens L3 by the light detector 4C for comparison. In this embodiment, the light detector 4C may be the same light detector as the light detector 5A of the above-mentioned receiving section 5, for example, a photodiode. A signal detected by this light detector 4C is fed back to a driving control circuit (not shown) of the foregoing light source 4A, compared with a set value, and conducts control so as to keep a constant amount of output light of the light source 4A.

FIG. 11 illustrates another embodiment of the projecting section 4 having substantially the same configuration as above shown in FIG. 10. The configuration of this embodiment is different from the projecting section 4 shown in FIG. 10 in that a short pass filter 43 is provided between the beam splitter 41 and the light source 4A.

Figure 3:
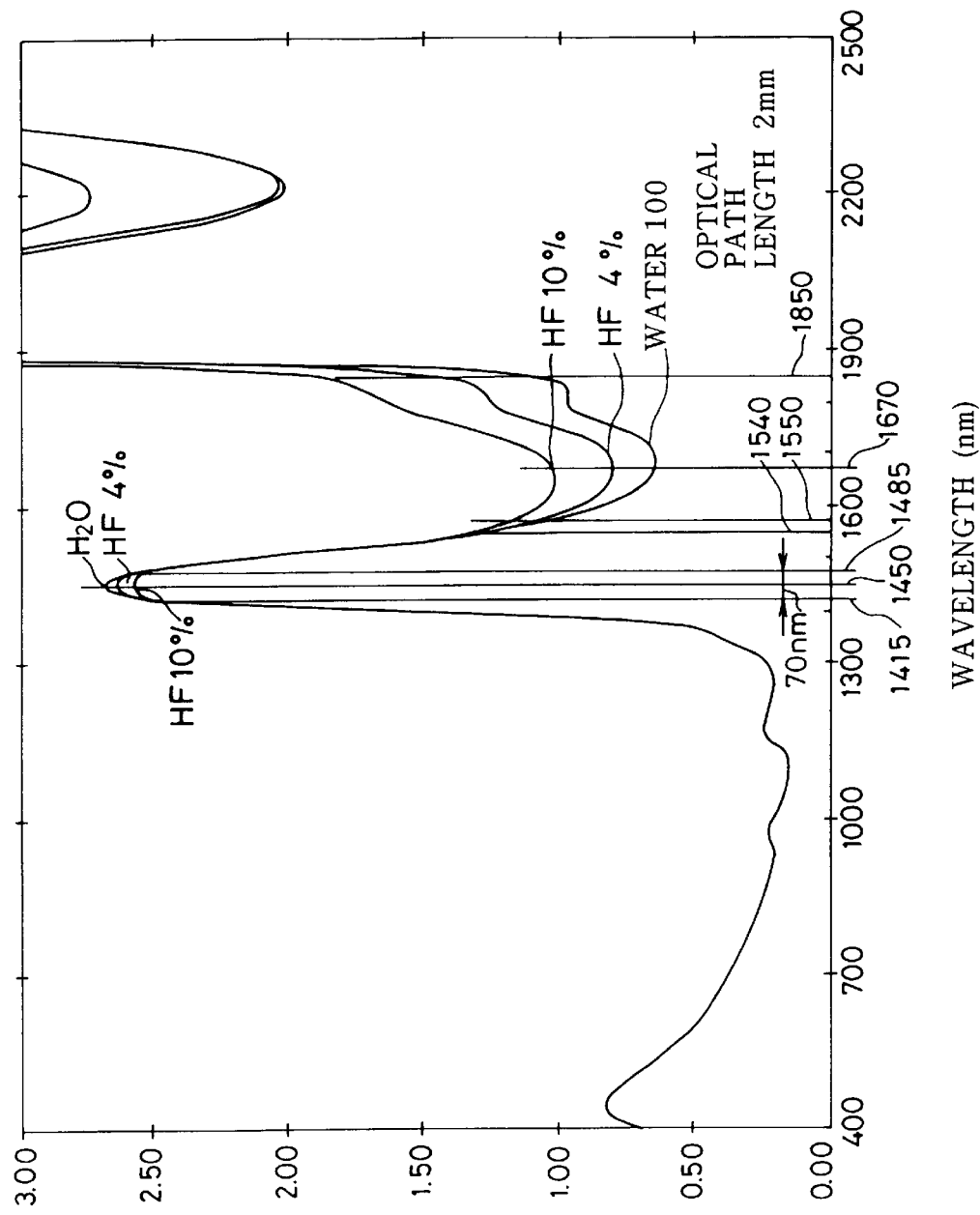
FIG. 3 is an absorption spectral diagram of hydrofluoric acid.
Figure 12:
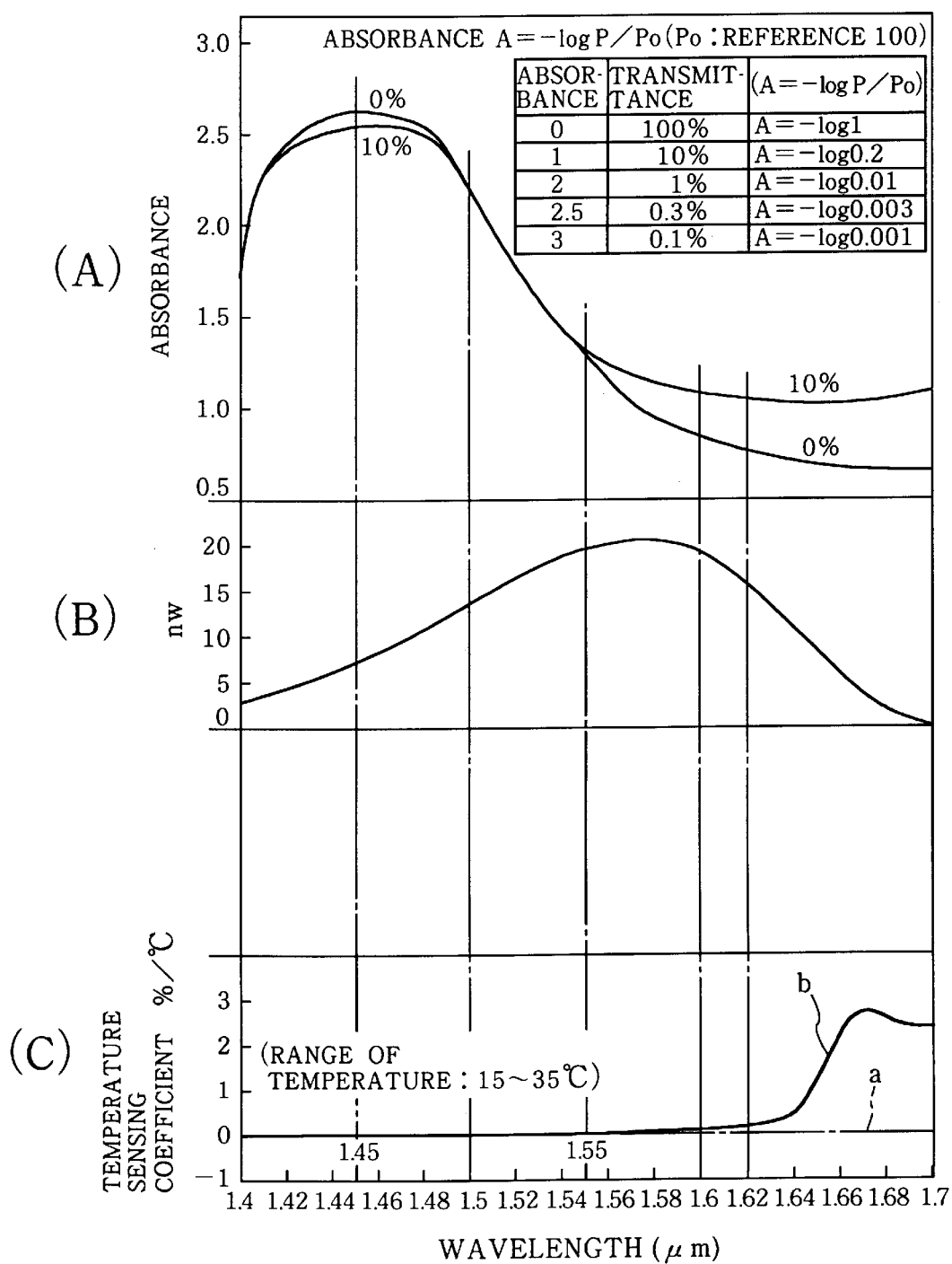
FIGS. 12 (A), (B) and (C) are graphs illustrating the absorption spectral diagram, the light output distribution and the temperature sensing property of an embodiment of the diode used as a light detector of the receiving section, respectively.
Figure 13:
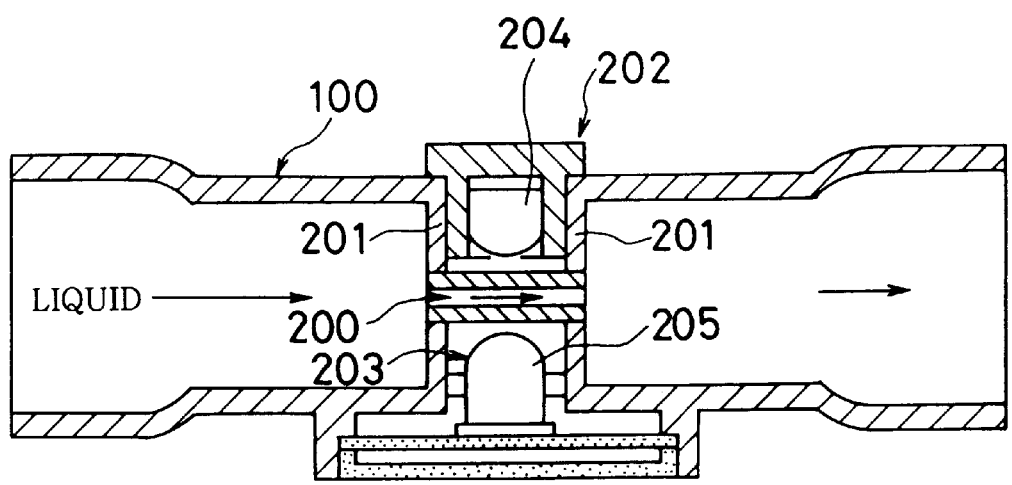
FIG. 13 is a schematic configuration diagram of a conventional concentration detecting apparatus.

FIG. 12 (A) is an enlarged view showing the wavelength region of 1.4 to 1.7 μm of the absorption spectral diagram of hydorfluoric acid as shown in FIG. 3. FIG. 12 (B) illustrates the light output (light amount) distribution in the case where a light-emitting diode (LED) (made by Shimazu company; product name: HK 9421-10) is used as the light source of the projecting section 4. As can be understood in FIGS. 12 (A) and 12 (B), it is preferable to use a wavelength of 1.55 μm or more or preferably, of 1.60 μm or more in which the difference among the light emitting rates becomes substantial and yet the light output remains high.

In addition, FIG. 12 (C) illustrates the temperature sensing characterristic of a photodiode used as the light detector 5A of the receiving section 5. Line (a) in FIG. 12 (C) shows the temperature sensing characteristic of an InGaAs-PIN photodiode (product name: G5851-01) made by Hamamatsu Photonics Co. which has a constant temperature sensing coefficient in a wavelength region within a range of from about 1.4 to 1.9 μm.

However, for example, an InGaAs-PIN photodiode (product name: G5832-01) made by Hamamatsu Photonics Co. has the temperature sensing characteristic as shown by line (b) in FIG. 12 (C). This suggests that this photodiode, showing a constant temperature sensing coefficient within a wavelength region of up to 1.62 μm, exhibits large fluctuations of temperature sensing coefficient for wavelengths of over 1.62 μm. When using a photodiode having such a characteristic as the light detector 5A for detecting a light having a wavelength region within a range of from 1.3 to 1.9 μm used in the present invention, and particularly of from 1.55 to 1.7 μm or from 1.6 to 1.7 μm in this embodiment, the measuring accuracy would largely vary with temperature.

The embodiment shown in FIG. 11 can resolve such problems. That is, in this embodiment, the short pass filter 43 cuts a wavelength over 1.62 μm from the light source 4A to prevent a light of such a wavelength from being detected by the light detector 5A of the receiving section 5. By adopting the projecting section 4 of this embodiment, it is possible to detect the concentration of the liquid always at a constant accuracy, irrespective of fluctuations of temperature.

In addition, according to a further embodiment a short pass filter (not shown) for cutting wavelength portions less than a prescribed wavelength, for example, less than 1.5 μm of the light emitted from the light source 4A, may be substituted for or newly added to the above mentioned short pass filter 43 in order to eliminate the influence of the absorption of the water in the atmosphere or the influence of the absorption of the water int he solution at a wavelength of near 1.45 μm.

When it is required to cut wavelength portions less than a prescribed wavelength and wavelength portions more than a prescribed wavelength, it is possible to use two short pass filters in combination as mentioned above, and also to use a band pass filter which can cut the wavelength portions less than a prescribed wavelength and the wavelength portions more than a prescribed wavelength.

By means of the liquid concentration detecting apparatus adopting the projecting section 4 of the foregoing embodiments, the concentration of hydrofluoric acid could continuously be measured at an accuracy of ±0.01%.

It is needless to mention that, when using, for example, a light-emitting diode as the light source 4A, the light-emitting diode itself provides a relative light output having temperature property. By providing a light detector for comparison 4C, as described above, it is possible to appropriately control fluctuations of the light intensity of the light source 4A. Further, by using a thermistor, it is desirable to compensate temperature characteristic of the foregoing photodiode 5A and to compensate temperature characteristic of relative light output of the light-emitting diode. As to the electric control circuit for this purpose, which is commonly known to persons skilled in the art, description is omitted here.

In the foregoing embodiment, measurement of concentration of hydrofluoric acid-based etching solutions (hydrofluoric acid (HF), buffered hydrofluoric acid (BHF), fluoronitric acid), of which measurement of concentration at an error range of ±0.1% or ±0.01% is considered difficult, has been described. The present invention is not however limited to hydrofluoric acid-based etching solutions, but applicable to aqueous solution of various substances such as hydrochloric acid, nitric acid, an alkaline etching agent, a chromic acid-based etching agent, phosphoric acid, ammonium hydroxide, hydrogen peroxide solution, and mixed water/organic liquidsolution (for example, aqueous acetic acid solution).

According to the liquid concentration detecting apparatus of the present invention, as described above, the cell is provided with a spacer having a slender hole formed therein, and is configured to be substantially in close contact with the both surfaces of the spacer at least within a detecting region where the projecting section and the receiving section are arranged opposite to each other, whereby the liquid supplied to the cell flows through the slender hole formed in the spacer in the detecting section. It is therefore possible to achieve a real-time and high-accuracy detection of the concentration of a liquid used in a semiconductor plant with a simple configuration at a low cost, thus providing industrially useful effects.

We claim:

1. An apparatus for detecting the concentration of an etching or cleaning solution comprising:
   (a) a cell having an axial line, the cell supplied with a solution selected from the group consisting of hydrofluoric acid, buffered hydrofluoric acid, fluoronitric acid, sulfuric acid, ammonium hydroxide, a mixed water/organic liquid solution, hydrofluoric acid-based solution, hydrochloric acid, nitric acid, chromic acid, phosphoric acid, hydrogen peroxide solution, and alkaline etching agent;
   (b) a projecting section and a receiving section arranged opposite to each other in a direction at right angles to the axial line of the cell;
   (c) a first light source disposed in the projecting section to project light from said projecting section through the solution in the cell to the receiving section, the light source having a central wavelength within a range of 1.54 to 1.85 $\mu$m; and
   (d) a light detector in the receiving section arranged to detect the light received by the receiving section, the amount of light detected providing an indication of the concentration of the solution.

2. The apparatus according to claim 1, wherein the projecting section comprises:
   a beam splitter for splitting the light emitted from the light source into first and second directions;
   a lens system for projecting the light emitted from the light source in the first direction through the beam splitter and through the cell, as a parallel beam to said cell; and
   a light detector for detecting the light emitted in the second direction,
   wherein the light emitted from the light source is controlled to a constant intensity based on the amount of light detected by the light detector detecting light emitted in the second direction.

3. The apparatus according to claim 2, wherein the projecting section further comprises a second light source for emitting light having a wavelength within a range from 0.4 $\mu$m to 1.1 $\mu$m.

4. The apparatus according to claim 3, wherein the first light source is one of a light-emitting diode and a laser diode emitting light having a central wavelength of 1.55±0.05 $\mu$m, and said second light source is a light emitting diode emitting light having a central wavelength of 0.94±0.05 $\mu$m.

5. The apparatus according to claim 4, wherein at least the first light source is turned on intermittently.

6. The apparatus according to claim 4, wherein at least one light-emitting diode has an on-time/off-time ratio in the range from 1:99 to 1:200 and is turned on intermittently.

7. The apparatus according to claim 2, wherein the projecting section further comprises a second light source emitting light having a central wavelength within a range from 0.9 $\mu$m to 1.0 $\mu$m.

8. The apparatus according to claim 2, wherein the projecting section has a Peltier element cooling mechanism.

9. The apparatus according to claim 2, wherein a short pass filter for blocking wavelengths greater than a prescribed wavelength of the light emitted from the light source is provided between the light source and the beam splitter.

10. The apparatus according to claim 9, wherein the projecting section further comprises a second light source for emitting a light having a wavelength within a range from 0.4 $\mu$m to 1.1 $\mu$m.

11. The apparatus according to claim 10, wherein the first light source is one of a light-emitting diode and a laser diode emitting light having a central wavelength of 1.55±0.05 $\mu$m, and said second light source is a light emitting diode emitting light having a central wavelength of 0.94±0.05 $\mu$m.

12. The apparatus according to claim 11, wherein at least the first light source is turned on intermittently.

13. The apparatus of claim 12, wherein at least one light-emitting diode has an on-time/off-time ratio in the range from 1:99 to 1:200 and is turned on intermittently.

14. The apparatus according to claim 9, wherein the projecting section further comprises a second light source emitting light having a central wavelength within a range from 0.9 $\mu$m to 1.0 $\mu$m.

15. The apparatus according to claim 9, wherein the projecting section has a Peltier element cooling mechanism.

* * * * *